United States Patent [19]

Bader et al.

[11] Patent Number: 5,041,291

[45] Date of Patent: Aug. 20, 1991

[54] BIODEGRADABLE POLY(HYDROXYALKYL)AMINO DICARBOXYLIC ACID) DERIVATIVES, A PROCESS FOR THEIR PREPARATION, AND THE USE THEREOF FOR DEPOT FORMULATIONS WITH CONTROLLED DEIVERY OF ACTIVE INGREDIENT

[75] Inventors: Hubert Bader, Mainz; Diether Rüppel; Axel Walch, both of Frankfurt am Main, all of Fed. Rep. of Germany

[73] Assignee: Hoechst Aktiengesellschaft, Frankfurt am Main, Fed. Rep. of Germany

[21] Appl. No.: 402,609

[22] Filed: Sep. 5, 1989

Related U.S. Application Data

[63] Continuation of Ser. No. 140,132, Dec. 31, 1987, Pat. No. 4,906,473.

[30] Foreign Application Priority Data

Jan. 3, 1987 [DE] Fed. Rep. of Germany ....... 3700128

[51] Int. Cl.$^5$ .............................................. A61K 9/14
[52] U.S. Cl. .................... 424/426; 424/444; 424/464; 424/486; 424/489
[58] Field of Search ............... 424/426, 464, 444, 486, 424/489

[56] References Cited

U.S. PATENT DOCUMENTS

| | | | |
|---|---|---|---|
| 4,451,452 | 5/1984 | Deibig et al. ..................... | 424/81 X |
| 4,800,085 | 1/1989 | Yoshida et al. .................... | 424/462 |
| 4,892,733 | 1/1990 | Bichon et al. ...................... | 424/422 |

Primary Examiner—Thurman Page
Assistant Examiner—James M. Spear

Attorney, Agent, or Firm—Finnegan, Henderson, Farabow, Garrett, and Dunner

[57] ABSTRACT

The invention relates to biodegradable poly((hydroxyalkyl)amino dicarboxylic acid) derivatives of the formula I

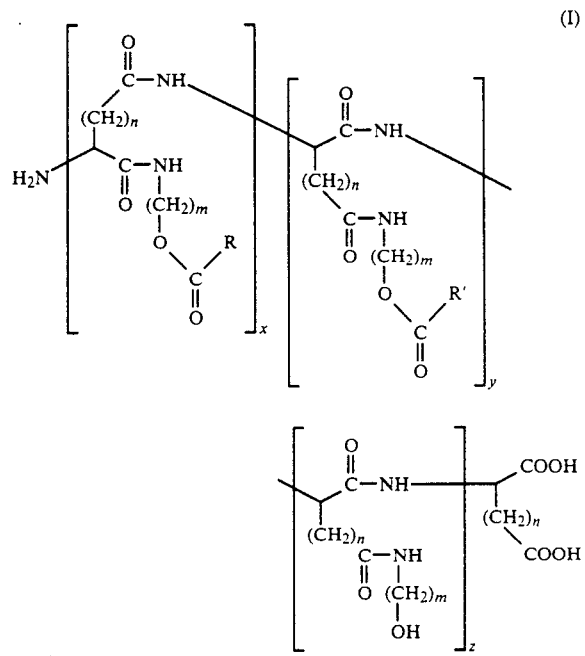

in which n, m, x, y, z, R and R' have the indicated meanings, and to a process for their preparation and to the use thereof for depot formulations with controlled delivery of active ingredient.

4 Claims, 1 Drawing Sheet

BIODEGRADABLE POLY(HYDROXYALKYL)AMINO DICARBOXYLIC ACID) DERIVATIVES, A PROCESS FOR THEIR PREPARATION, AND THE USE THEREOF FOR DEPOT FORMULATIONS WITH CONTROLLED DEIVERY OF ACTIVE INGREDIENT

This is a continuation of application Ser. No. 140,132 filed Dec. 31, 1987 now U.S. Pat. No. 4,906,473.

The invention relates to biodegradable poly(hydroxyalkyl-amino dicarboxylic acid) derivatives, to a process for their preparation and to the use thereof for depot formulations with controlled delivery of active ingredient. This entails the active ingredients being embedded in a matrix composed of the polyamides according to the invention, and undergoing controlled release in vivo due to bioerosion of the matrix. Degradation of the products according to the invention results solely in fragments which are endogenous or whose biocompatibility is known, and which are metabolized by natural transformation routes or, by reason of their solubility in water, are excreted via the kidneys.

Modern drug therapy demands, especially for the administration of active ingredients, new presentations which combine a controlled rate of delivery of the active ingredient with high biocompatibility of the depot. In human and veterinary medicine there is great current interest in long-lasting, controlled delivery of active ingredients because of the increasing importance of chronic diseases and therapeutic policies oriented to the long term. Biodegradable polymers are particularly advantageous as matrix materials for depot systems of this type, because the bioerosion controls the release of active ingredients and allows surgical removal of such a depot to be dispensed with.

Drug delivery systems in which the active ingredient is dispersed in a non-degradable polymer matrix and is released by diffusion are described in U.S. Pat. No. 4,069,307. However, after the active ingredient reservoir has been exhausted, it is necessary for implants of this type to be surgically removed from the body.

In biodegradable medicament delivery systems, as specified in U.S. Pat. No. 4,093,709, the active ingredient is dispersed in a biodegradable polymer which releases the active ingredient on degradation. Typical biodegradable polymers, which have undergone most investigation in the state of the art, are homo- and copolyesters, in particular of lactic and glycolic acid, as described in U.S. Pat. Nos. 3,773,919 and 3,297,033. It is a disadvantage that, inter alia, the swellability of the polyesters in a physiological medium is low or difficult to control, which hinders the transport of the active ingredients incorporated in the implant through the polymer matrix to the surface, and results, after an initial burst effect, in only a low rate of release.

Recently, polyacetals and -ketals (U.S. Pat. No. 4,304,767) and polyanhydrides (H. G. Rosen et al., Biomaterials 4, 131 (1983)) and polyorthoesters (U.S. Pat. No. 4,180,646), which were developed as biodegradable polymers for use as implant materials, have been described.

These polymers resemble the polyesters mentioned in that their degradation is determined only by the resistance of the carbonyl group in the main chain of the polymer to hydrolysis, and can be influenced slightly only by incorporation of comonomers. Moreover, polymers of this type do not have sufficient stability for implantation lasting months.

Another class of polymers which have been described, in U.S. Pat. No. 3,371,069, as bioabsorbable implant materials are polyamides, in particular poly($\alpha$-L-amino acids). However, industrial production of poly(amino acids) requires the use of costly protected amino acids, large amounts of highly toxic phosgene, the elimination of the protective groups and the subsequent derivatization of the resulting polymers.

A further disadvantage of polyamides of this type is the presence of charged groups due to incomplete derivatization in the synthesis of the implant material, and the additional generation of such ionic groups due to bio-erosion in the body. The pure poly-L-glutamic acid and pure poly-L-lysine which are mentioned in the patents are toxicologically extremely unacceptable (A. D. Kenny, Proc. Soc. Exp. Biol. Med. 100, 778 (1959)) and hence their copolymers, which result from hydrophobic derivatives by biodegradation, must likewise be regarded very critically.

U.S. Pat. No. 4,356,166 describes biodegradable implant materials which release in vivo a bioactive compound. The bioactive compounds described in U.S. Pat. No. 4,356,166 are progestins which are initially chloroformylated and then covalently bonded to the polymer. The polymers used for this are poly((hydroxyalkyl)-L-glutamine) or poly((hydroxy-alkyl)-L-aspartamide). The bioactive compounds are bonded either via a so-called spacer group or directly via the reactive component of the polymer. The rate of release of the bioactive compound is controlled by the molecular weight of the polymer or by the length and the nature of the spacer group.

The disadvantage of these substances claimed in U.S. Pat. No. 4,356,166 is that they themselves are drugs with high pharmacological activity. In polymer/active ingredient conjugates of this type (polymeric drugs), the biocompatible polymer and active ingredient form a unit whose properties are determined in a complex manner by the two components. The rate of release of the bioactive molecule which is attached to the polymer can be varied within the scope of the abovementioned parameters but crucially depends on the nature of the active ingredient. Hydrophobic bioactive substances such as, for example, steroid hormones can be only very slowly cleaved off the polymer backbone in an aqueous biological medium and are thus suitable only for extremely long-term depot forms. For each active ingredient, new polymer/active ingredient conjugates must be synthesized, which greatly limits the applicability of the concept of drugs attached to polymers which is described in U.S. Pat. No. 4,356,166.

For these reasons, these substances are unsuitable for use as polymers which can undergo controlled degradation and which, due to their own biodegradation, release an active ingredient which is embedded in the inert polymer matrix without having to be chemically bonded to the polymer for this.

Poly((hydroxyalkyl)amino dicarboxylic acid) derivatives which, surprisingly, are outstandingly suitable for use as degradable medicament implants with controlled delivery of active ingredients have now been synthesized. The essential feature of this invention is that the active ingredients do not have to be chemically bonded to polymer but are merely embedded in this polymer matrix. It is possible, by incorporating suitable biologically inactive acyl groups, to control, in the desired manner, the rate of degradation of the polymer in vivo, and thus also the rate of release of the active ingredient. The advantage of this procedure is that it is now possible to administer, over a prolonged period with a relatively constant dose, even those active ingredients which either cannot by any means be bonded chemically to a polymer or are too sensitive to survive the conditions for the chemical coupling to the polymer, which are, after all, rather drastic. In addition, in principle the polymers can be used universally as pharmacologically inert matrix for all relevant drugs, irrespective of the molecular size and other physicochemical parameters. These biodegradable polymers are obtained by polycondensation of amino dicarboxylic acids, with subsequent reaction with amino alcohols to give poly(-hydroxyalkyl)amino dicarboxylic acids), and then with carboxylic acids, carbonyl halides or halogenoformic esters in a polymer-analogous acylation to give the desired poly(hydroxyalkylamino dicarboxylic acid) derivatives. In vivo, these polymers are metabolized to non-toxic, non-allergenic and non-immunogenic compounds and are excreted.

BRIEF DESCRIPTION OF THE DRAWINGS

The sole FIGURE is a plot of the percent buserelin delivered as a function of time.

Thus the invention relates to:

Figure 1:
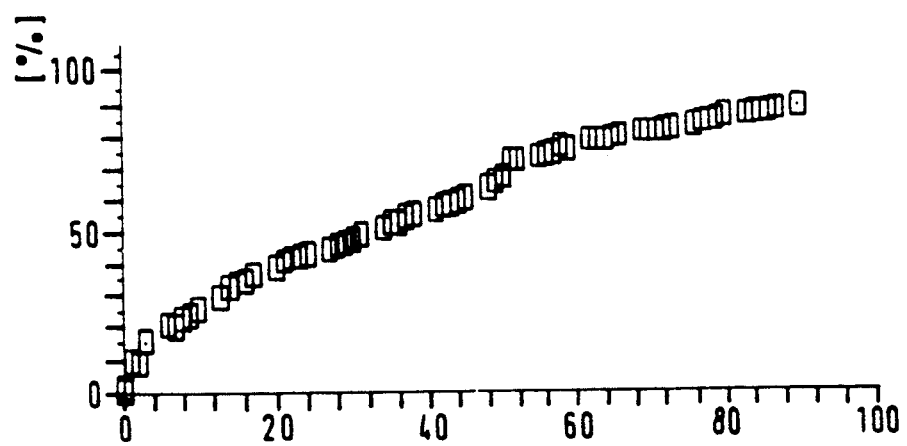

Poly((hydroxyalkyl)amino dicarboxylic acid) derivatives of the formula I

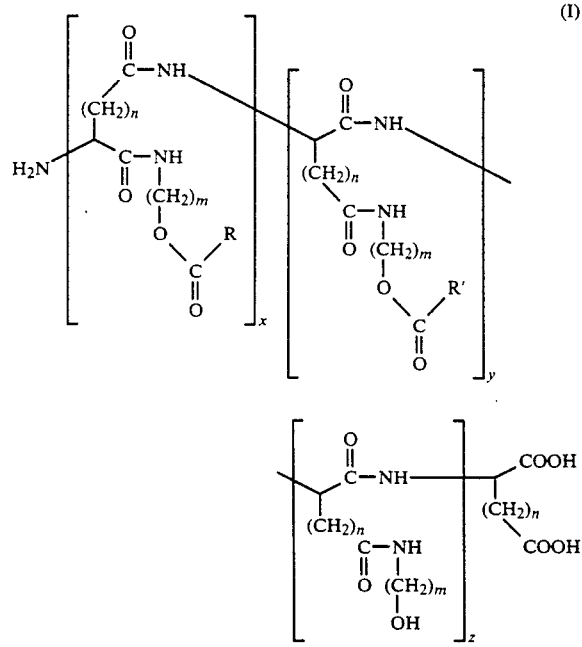

in which n is 1 or 2, m is 2 to 6, x and y are 1 to 400, and z is 0 to 40, wherein the radicals R and R' are identical or, independently of one another, different and denote branched or unbranched, saturated or unsaturated alkyl, cycloalkyl, alkyloxy or cycloalkyloxy having a total of 1–22 carbon atoms in the alkyl moiety, it being possible for the alkyl moiety optionally to be interrupted by a carbonyloxy group, or biologically inactive steroid alcohols bonded via their hydroxyl groups, there being random distribution in the polymer of the monomer units placed in square brackets.

The invention also relates to the process for the preparation of the abovementioned polyamides and to their use, also in mixtures with other biocompatible polyamides, especially combined with biologically active substances, as degradable active ingredient depot formulation with controlled delivery of active ingredient.

The invention is described in detail hereinafter.

Amino dicarboxylic acids which can be used are aspartic acid (n=1) or glutamic acid (n=2).

It is preferable to use aspartic acid, which reacts in a polycondensation reaction to give the corresponding polyanhydroaspartic acid (VII). Reaction with an amino alcohol of the formula IV $$H_2N—(CH_2)_m—OH \quad\quad IV$$

in which m is a number from 2 to 6, preference being given to 3-aminopropanol, and especially to 2-aminoethanol, results in α,β-poly((hydroxyalkyl)-DL-aspartamide) of the formula II

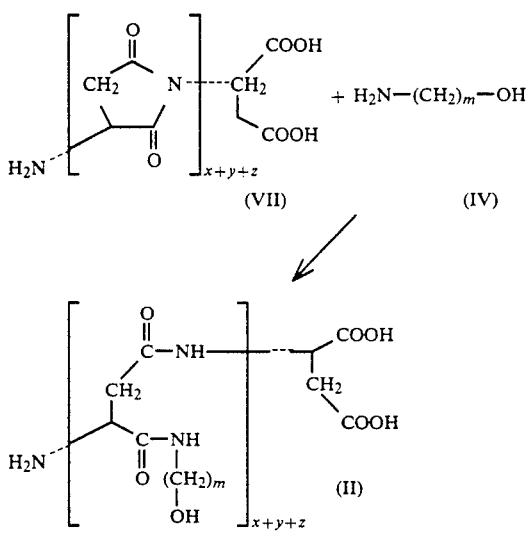

A process for the preparation of α,β-poly((2-hydroxyethyl)-DL-aspartamide) (PHEA) is described by P. Neri, G. Antoni, F. Benvenuti, F. Cocola, G. Gazzei in J. Med. Chem. 16, 893 (1973). A general procedure for the preparation of PHEA is to be found in P. Neri, G. Antoni. Macromol. Synth. 8, 25. Explicit reference is made at this point to the citation. The reaction takes place in high yield to give a product of high purity. It is possible in the same way to prepare the analogous higher amino alcohol derivatives of polyanhydroaspartic acid.

It is necessary, for the preparation of poly((hydroxyalkyl)-L-glutamine), to use a different, more complicated process, as described in U.S. Pat. No. 4,356,166. This entails, in the first place, the γ-COOH group of L-glutamic acid being protected by esterification with benzyl alcohol. This γ-benzyl glutamate is then converted by N-carboxylation with phosgene into an anhydride which then, after addition of triethylamine in an inert solvent, polymerizes, resulting in poly((γ-benzyl)L-glutamate). The protective group is eliminated either by addition of an HCL/HBr mixture, to give the free poly-α-L-glutamic acid, or in the presence of hydroxyalkylamines to give the analogous poly-((α-hydroxyalkyl)-L-glutamines). A general procedure for the preparation of poly(α-(hydroxypropyl)-L-glutamine is to be found in U.S. Pat. No. 4,356,166, to which explicit reference is made at this point. The analogous higher amino alcohol derivatives of poly((γ-benzyl)L-glutamate) can also be prepared in the same way.

These poly((hydroxyalkyl)amino dicarboxylic acids) of the formula IIa

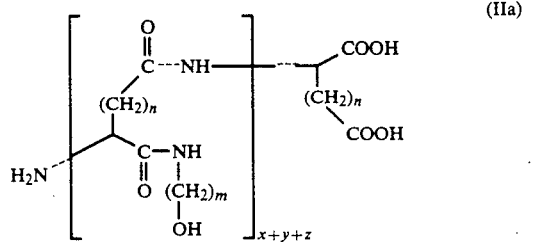

preferably α,β-poly((hydroxyalkyl)-DL-aspartamide) are now, according to the invention, reacted in the subsequent reaction step with one or more different biologically inactive compounds of the formula V and-/or VI

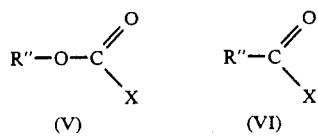

to give the poly((hydroxyalkyl)amino dicarboxylic acid) derivatives according to the invention. In these formulae, X represents a leaving group which allows esterification of the alcoholic group on the polymer under mild conditions. Preferred are chlorine, bromine, iodine, imidazolides, anhydrides or hydroxyl, especially chlorine. Suitable radicals R" are alkyl or cycloalkyl groups having a total of 1-22 carbon atoms in the alkyl radicals. It is preferable to use in homopolymers alkyl radicals having 5-22 carbon atoms, in particular those having 6-18 carbon atoms. Particularly preferred in compounds of the formula V are those alkyl radicals R" having an even number of carbon atoms, and in compounds of the formula VI those alkyl radicals R" having an odd number of carbon atoms. It is also possible for the preparation of copolymers, that is to say in the reaction with two or more different compounds of the formula V and/or VI, to use compounds with shorter alkyl radicals than indicated as the preferred ranges. Thus, for example, 50 mol-% of a compound having a C-8 alkyl chain can be reacted with 50 mol-% of a compound having a C-2 alkyl chain to give the poly(hydroxyalkylamino dicarboxylic acid) derivatives.

The said alkyl radicals can be branched, but are preferably unbranched. It is likewise possible to use unsaturated alkyl radicals, but saturated are preferred. Furthermore, it is possible for the alkyl radical also to be interrupted by a carbonyloxy group. Also suitable as R" are steroid radicals, especially cholesteryl.

The reaction with the compounds of the formula type V or VI can take place both with a single compound of this type and with any desired combinations of these compouds, as well as with compounds which have different radicals R", for example differing in the nature of their branching and, in particular, in their chain length.

The polymer-analogous acylation which was mentioned last is carried out by known processes of organic chemistry as described in, for example, Houben-Weyl, Methoden der Organischen Chemie, (Methods of Organic Chemistry), Vol. VIII/3, pages 543 et seq., G. Thieme Verlag, Stuttgart, (1952). It takes place selectively on the hydroxyl group to give esters or carbonates, without attacking other groups in the initial polymer. The Einhorn variant of the Schotten-Baumann acylation in the presence of pyridine is particularly suitable. Using this, very high degrees of derivatization (greater than 70%) are achieved under mild conditions.

Where the degrees of derivatization are below 100%, i.e. where free hydroxyl groups are still present, and in the case where different substituents R and R' are incorporated in the polymer, it is possible for the polymer to be constructed of up to three different monomer units (placed in square brackets in formula I), which are then randomly distributed in this polymer.

A homopolymer is produced on acylation with only one substance of formula V or VI and where the degrees of derivatization are 100%.

The molecular weight of the polymers according to the invention is 200 to 90,000 (for $x+y+z=2$ up to 840, and with a molecular weight of about 100), preferably 20,000 to 84,000 (for $x+y+z=200$ to 840). The proportion of the hydroxyalkylamino dicarboxamide monomer unit—based on the molar proportion of the acylated amino dicarboxamides—ought not to exceed 30 mol-%, preferably 10 mol-% (i.e. $z=0$ to 40).

Among the carbonyl halides and halogenoformic esters, the chlorine compounds are preferred.

The chloroformic esters which are preferably used as starting substances are obtained by reaction of phosgene with the appropriate biologically inactive, physiologically acceptable, aliphatic or cycloaliphatic, in particular unbranched, alcohols. The alcohols which are particularly preferably used are those which have an even number of carbons. The chloroformylated steroids are also obtained in this way. Thus, in principle, all biologically inactive steroids having reactive hydroxyl groups are accessible. Examples which may be mentioned here are: cholesterol, cholestanol, coprostanol, ergosterol, sitosterol or stigmasterol.

The acid chlorides which can be used, and are likewise preferred, as starting compounds are obtained, for example, from the corresponding carboxylic acids by reaction with phosphorus trichloride, phosphorus pentachloride, oxalyl chloride or thionyl chloride (Houben-Weyl, Meth. d. Org. Chem., 4th ed., Vol. VIII, pages 463 et seq., Thieme Verlag Stuttgart 1952; and Houben-Weyl, Meth. d. Org. Chem. 4th ed., Suppl. Vol. E5, pages 587 et seq., Thieme Verlag Stuttgart, 1985).

Compounds of the formula type V or VI in which an alkyl chain is interrupted by a carbonyloxy group are prepared, for example, by reaction of cyclic dicarboxylic anhydrides with alcohols. The dicarboxylic monoesters obtained in this way are then reacted, in analogy to the carboxylic acids described above, for example with oxalyl chloride to give the corresponding acid chlorides.

The hydrophobicity of the poly((hydroxyalkyl)amino dicarboxylic acid) derivatives—and thus the time for which an implant prepared therefrom is retained in the body—can be adjusted within wide limits both by the number of carbon atoms in the acylating agent and by the degree of substitution. Thus, 6 carbon atoms or more in the alkyl moiety are sufficient to make the corresponding derivatives insoluble in water.

However, it is possible only with difficulty to state accurately the relation between the chain length and the degradation time in vitro/vivo, because the degradation time depends not only on the chain length but also on a large number of other parameters; for example on the particle size and distribution, the production method, for example of microspheres, the porosity of the microspheres, the temperature or the degradation medium.

The degree of substitution can be altered via the stoichiometry of the substances used in the acylation reaction, but ought preferably to be kept within the scope of the maximum yield (greater than 70%), i.e. the greatest possible percentage of the substitutable OH groups on the polymer framework ought to be esterified. If a lower degree of substitution is desired, the concentration of the acylating agent relative to the polymer is reduced correspondingly.

On degradation of these polyamides in vivo, the ester is cleaved again, resulting in the corresponding biologically inactive carboxylic acids and alcohols and poly(-hydroxyalkylamino dicarboxylic acid). This degradation under physiological conditions ought ideally to produce solely fragments which are endogenous or are known to be highly biocompatible and which are metabolized by natural transformation routes or, by reason of their solubility in water, are excreted via the kidneys. The biocompatible carboxylic acids and alcohols include those having 6–22 carbon atoms in the alkyl moiety, especially those having an even number of carbon atoms, or the biologically inactive steroids, such as, for example, cholesterol. In particular, the polymer, preferably the neutral PHEA, is formed again, which is highly soluble because of its strong interaction with water.

The new polymers differ particularly in this respect from derivatives of poly($\alpha$-amino acids) which have also been used experimentally in implants, such as, for example, poly-$\alpha$-L-glutamic esters, from which polyelectrolytes are produced by biodegradation and may, especially on repeated implantation, give rise to toxicological and immunological complications.

The presence of $\alpha$- and $\beta$-peptide bonds in D and L forms in the $\alpha,\beta$-poly((hydroxyalkyl)-DL-aspartamide) derivatives which are preferably used prevents the formation of organized structures (for example folded or helical regions) in the polymer, which influence the biodegradation in an unpredictable manner.

The partial rigidity caused by the amide bonds and brought about by the bridging hydrogen bonding (N . . . H. . . O) is the reason for a number of industrial processing advantages of this class of polymers according to the invention. Acylation with suitable reactive carboxylic acids on the hydroxyalkyl group of the polymer results in hydrophobic polyamides (when the alkyl moiety has at least 6 carbon atoms) which dissolve in a large number of organic solvents and can be converted into films from the solutions. The polyamides according to the invention are thermoplastic and are thus suitable for the preparation of active ingredient depot forms by various methods such as, for example, by compression, extrusion, precipitation, spraying etc.

It is possible, by known methods, to produce from the polyamides according to the invention implantable particles, in particular microcapsules and microspheres and, by compaction, microscopic shaped articles of any desired geometry, in particular tablets and rods.

The polyamide can, for example, be dissolved with the active ingredient in a suitable polar aprotic solvent, for example dimethyl sulfoxide or dimethylacetamide. The solution is, with the addition of an emulsifier, emulsified in an oily phase (for example paraffin) at a temperature at which the polymer solution is liquefied. After a few minutes, the individual solvent/polymer droplets are caused to solidify by cooling the emulsion. The polymer beads are hardened by washing with a suitable solvent in which the solvent used to dissolve the polyamide, as well as the oily phase, dissolve, but the polymer droplets do not. During this the volume of the beads decreases, but the shape does not change.

The excellent solubility of the polyamides according to the invention in organic solvents also makes it possible to produce microspheres by forming droplets from a solvent having a high melting point in a condensed cold gas, for example liquid nitrogen, the Leidenfrost phenomenon resulting in absolutely spherical particles. The high-melting and water-miscible solvent is dissolved out, and the polymer is simultaneously precipitated out, by transferring the microspheres into water, the spherical shape of the polyamide microspheres being retained.

If the organic solvent which is used has not only a high melting point but also a low boiling point, this droplet-forming process can be further simplified because the solvent, for example tert.-butanol, can be removed, directly, under mild conditions and without losses of active ingredient, by freeze-drying of the microspheres obtained by dropwise addition to liquid nitrogen.

The solubility of the polyamides according to the invention in many solvents, including those tolerated physiologically, for example alcohols, has particularly advantageous effects in the processing to microspheres by spray-drying. Thus, with the polyamides according to the invention it is possible to dispense with the use of toxicologically unacceptable halogenated hydrocarbons, such as are required for the spray-drying of biodegradable polyesters. Furthermore, their solubility in alcohols/water mixtures also permits the production of monolithic microspheres which contain active ingredient, because polymer and active ingredient can be sprayed from a molecular disperse form for this.

The polyamides according to the invention can also be used as mixtures and in mixtures with other biodegradable and/or biocompatible polymers (for example ®Pluronic F68, PHEA, dextrans, polyethylene glycols, hydroxyethylstarches and other degradable or excretable polysaccharides) or physiologically acceptable auxiliaries (for example polymer plasticizers).

Degradation tests in vitro on the polyamides according to the invention have shown that the rate of degradation can be regulated in a controlled manner via the functional side groups.

The invention is described in detail in the examples which follow. Unless otherwise indicated, percentage data relate to weight.

EXAMPLE 1

Preparation of
$\alpha,\beta$-poly((2-cholesteryloxycarbonyloxyethyl)-DL-aspartamide)

3.16 g (20 mmol) of $\alpha,\beta$-poly((2-hydroxyethyl)-DL-aspartamide) (PHEA) are dissolved in 50 ml of dry N,N-dimethylformamide (DMF). After addition of 2 g (25 mmol) of pyridine, the mixture is cooled to 0° C. and, while stirring, 11.23 g (25 mmol) of cholesteryl chloroformate are added within 10 minutes. The mixture is subsequently stirred at room temperature for 2 hours and then poured into 500 ml of ether. The precipitated product is filtered off with suction, washed with ether, acetone, water, acetone and ether and dried in vacuo. 6.5–7 g of a brownish white polymer which has a degree of substitution of about 80%, dissolves in DMF and dichloromethane/methanol and decomposes above 250° C. are obtained.

EXAMPLE 2

Preparation of α,β-poly((2-acetylethyl/2-octanoylethyl)-DL-aspartamide)

3 g (30 mmol) of pyridine are added to 3.16 g (20 mmol) of PHEA, dissolved in 20 ml of DMF, and the mixture is cooled to 0° C. While stirring, 0.79 g (10 mmol) of acetyl chloride is added dropwise, and the mixture is subsequently stirred at room temperature for 30 minutes. It is then again cooled to 0° C., and 3.25 g (20 mmol) of octanoyl chloride are added dropwise. The mixture is subsequently stirred at room temperature for 2 hours, poured into 500 ml of ether, and the product is filtered off with suction. For further purification, it is dissolved in methanol, precipitated by dropwise addition to 10% strength aqueous acetic acid solution, filtered off with suction, washed thoroughly with water and dried in vacuo. 5 g of a thread-forming, almost white polymer which dissolves in DMF, dichloromethane/methanol and methanol and melts above 180° C. are obtained.

EXAMPLE 3

3.16 g (20 mmol) of PHEA are reacted with 4.77 g (25 mmol) of 2-cyclohexylethyl chloroformate as indicated in Example 1. About 5 g of a pale yellow-colored thermoplastic polymer are obtained, in which free primary alcohol groups are no longer detectable by NMR spectroscopy (degree of substitution greater than 90%).

EXAMPLE 4

3.16 g (20 mmol) of PHEA are reacted with 9 g (25 mmol) of docosanoyl chloride as indicated in Example 1. The resulting polymer (about 8 g) is thermoplastic and dissolves in dichloromethane and tetrahydrofuran.

EXAMPLE 5

The acid chloride used for the reaction (n-butyl 4-chloro-4-oxobutyrate) is prepared in the following way: excess oxalyl chloride and one drop of DMF are added to monobutyl succinate, the reaction commencing with evolution of gas. The mixture is left to stand overnight with exclusion of moisture, and then the excess oxalyl chloride is removed in a rotary evaporator at 40° C. The product has IR bands at 1800 cm$^{-1}$ (acid chloride) and 1740 cm$^{-1}$ (ester) of equal intensity and is used, because of its instability, without further purification.

3.16 g (20 mmol) of PHEA are reacted with 4.82 g (25 mmol) of n-butyl 4-chloro-4-oxobutyrate as described in Example 1. Free primary alcohol groups are no longer detectable in the resulting polymer by NMR spectroscopy.

EXAMPLE 6

4.76 g (25 mmol) of mono-n-octyl succinate and 120 mg of DMAP (4-dimethylaminopyridine) are added to 3.16 g (20 mmol) of PHEA in 30 ml of DMF, and the solution is cooled to 0° C. and subsequently a solution of 5.2 g (25 mmol) of DCC (dicyclohexylcarbodiimide) in 20 ml of DMF is added dropwise. After stirring at 0° C. for 15 min, the reaction is allowed to continue at RT overnight, and then the precipitated dicyclohexylurea is filtered off, and the filtrate is concentrated to about 20 ml in a rotary evaporator. The polymer is precipitated by dropwise addition of the DMF solution to 500 ml of ether.

EXAMPLE 7

3.16 g (20 mmol) of PHEA are reacted with 6.15 g (25 mmol) of tetradecanoyl chloride in analogy to Example 1. The resulting pale brownish polymer (about 5.1 g) is thermoplastic and dissolves in dichloromethane and tetrahydrofuran.

EXAMPLE 8

3.16 g (20 mmol) of PHEA are reacted with 4.05 g (20 mmol) of octanoyl chloride in analogy to Example 1. The resulting yellowish white polymer (about 4.8 g) is thermoplastic and dissolves in dichloromethane and tetrahydrofuran.

EXAMPLE 9

In analogy to Example 2, 0.91 g (10 mmol) of methoxycarbonyl chloride and 3.24 g (20 mmol) of octanoyl chloride are added to 3.16 g (20 mmol) of PHEA. The resulting yellowish-white polymer (about 5.0 g) is thermoplastic and dissolves in dichlomethane and tetrahydrofuran.

EXAMPLE 10

Production of Microspheres 40 mg of $C_{14}$-PHEA from Example 7 are dissolved in 1 ml of methylene chloride/methanol (50/1 parts by volume). 10 mg of buserelin are added to the solution and dispersed using ultrasound. The dispersion is introduced into a beaker containing 60 ml of a stirred (800 rpm) 0.1% by weight aqueous polyvinyl alcohol solution (®Mowiol 28–99) saturated with 0.3 ml of methylene chloride/methanol (50/1).

After 5 minutes, the contents are poured into a beaker containing 200 ml of water, and the mixture is stirred (200 rpm) for 30 minutes. The supernatant water is decanted off, and the microspheres are lyophilized (diameter after lyophilization: 20–90 μm).

EXAMPLE 11

Production of Microspheres 44 mg of $C_2$–$C_8$-PHEA from Example 2 are dissolved in 100 ml of dimethyl sulfoxide, and then 1,000 μl of methylene chloride are added.

The solution is introduced into a beaker containing 60 ml of a stirred (800 rpm) 0.1% by weight aqueous solution of carboxymethylcellulose (®Serva, 300 cps) at 4° C. which is saturated with 0.3 ml of methylene chloride. After 5 minutes, the contents are worked up as in Example 10.

EXAMPLE 12

Production of Microspheres 80 mg of $C_8$-PHEA from Example 8 are dissolved in 1 ml of dimethyl sulfoxide at 50° C., and 20 mg of hydroxypropylcellulose (®Klucel M) are added. The solution of the two polymers is added dropwise, using a needle (disposable syringe, external diameter of needle 0.6 mm), to a container of liquid nitrogen (100 ml).

The resulting microspheres are transferred into 200 ml of water, and residual solvent is extracted for 2 hours. Excess water is decanted off, and the micro-

EXAMPLE 12a

Production of Microspheres by Direct Freeze-Spraying from Tert.-Butanol 320 mg of $C_6$-PHEA are swollen in a little ethanol and dissolved in 3.6 g of tert.-butanol. 80 mg of micronized buserelin is dispersed in this solution by sonication, and the mixture is introduced as drops through a fine nozzle into liquid nitrogen. The liquid nitrogen is decanted, and the solvent is removed from the microspheres by immediate freeze-drying.

EXAMPLE 12b

Production of Microspheres by Spray-Drying 400 mg of polyamide from Example 5 are dissolved in 8 ml of 90% strength ethanol, and the solution is combined with 100 mg of PHEA and 100 mg of buserelin in 1 ml of water. The mixture is sprayed in a spray-drier to form microspheres.

EXAMPLE 13

Polymer Degradation

Determinations are carried out of the absorption of water (in % by weight) by various substituted polyhydroxyethylaspartamides after storage at 92% relative humidity for 74 h, and of the hydrolysis time of the alkyl ester/alkyl carbonate side groups (in hours) until 100 mg of each powdered polymer dissolves completely in 100 ml of aqueous NaOH (pH 13):

| Polymer | from example | absorption of water % | dissolution h |
|---|---|---|---|
| $C_8$—PHEA | 8 | 25 | 3 |
| $C_{14}$—PHEA | 7 | 8 | 200 |
| $C_2/C_8$—PHEA | 2 | 12 | 23 |
| $C_1C/C_8$—PHEA | 9 | 80 | 1 |

EXAMPLE 14

Polymer Degradation 3 samples, each of 500 mg of polymer, are each incubated in 30 ml of a phosphate buffer solution composed of 0.00205 mol of $Na_2HPO_4$ and 0.0045 mol of $NaH_2PO_4$ (pH 7.4) and the solutions are stirred in closed glass bottles (50 ml) at 37° C.

The phosphate buffer is stabilized against microbial attack with 0.0078 mol of $NaN_3$, and its pH is corrected every 7 days.

Over a period of 150 days the weight losses of the polymer samples are measured: the buffer solution with incubated polymer is filtered through a weighed glass frit, the residue is dried over phosphorus pentoxide in vacuo for 24 h, and the weight loss is determined.

| Polymer | from example | weight loss (%) 14 days | 70 days | 150 days |
|---|---|---|---|---|
| $C_8$—PHEA | 8 | 5 | 22 | 84 |
| $C_{14}$—PHEA | 7 | 0 | 5 | 21 |
| $C_2/C_8$—PHEA | 2 | 0 | 14 | 43 |
| $C_{10}/C_8$—PHEA | 9 | 11 | 65 | 100 |

EXAMPLE 15

Production of Rod-Like Implants ("Rods")

An intimate mixture of powdered polymers, additives and active ingredient(s) is heated in a suitable apparatus, for example an extruder for thermoplasts, above the softening point, resulting in a deformable mass. Additives and active ingredient(s) are homogeneously dispersed in the softened polymer by kneading, and the resulting polymer/active ingredient suspension is forced through a nozzle of suitable diameter (>0.5 mm). On cooling, the strand of extruded polymer/active ingredient suspension solidifies to a solid rod-like aggregate whose content of active ingredient is determined by its length and its diameter.

EXAMPLE 16

Active Ingredient Delivery (Release of Buserelin)

Microspheres composed of
88% by weight of LEMF
6% by weight of $C_2$-$C_8$-PHEA from Example 2
6% by weight of buserelin are prepared in analogy to Example 10. LEMF is poly-(lysine ethyl/methyl ester fumaramide), and German Patent Application No. 3,616,320.1 (Example 8) relates to it, and it is prepared, for example, by polycondensation of fumaroyl chloride,
lysine methyl ester dihydrochloride and
lysine ethyl ester dihydrochloride.

The delivery of active ingredient (buserelin release) is measured in a buffer solution (2.91 g of $Na_2HPO_4$, 0.540 g of $NaH_2PO_4$, 0.4 g of $NaN_3$, 6.328 g of NaCl and 2.52 g of $NaHCO_3$ in 1 l of water by UV spectroscopy. FIG. 1 is a plot of the total proportion (in percent) of buserelin delivered as a function of time.

We claim:

1. A method of preparing a biodegradable active ingredient depot formulation with controlled delivery of a biologically active ingredient which comprises incorporating a biologically active ingredient into a controlled release agent which contains a poly (hydroxyalkyl) amino dicarboxylic acid derivative of the formula I

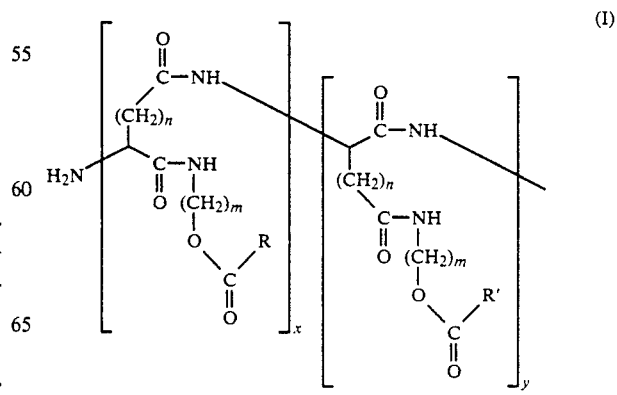

-continued

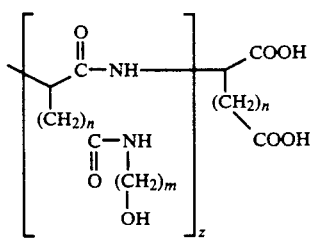

in which n is 1 or 2, m is 2 to 6, x and y are 1 to 400, and z is 0 to 40, and in which the radicals R and R' are identical or, independently of one another, different and denote branched or unbranched, saturated or unsaturated alkyl, cycloalkyl, alkoxy or cycloalkyloxy groups having a total of 1-22 carbon atoms in the alkyl moiety, the alkyl moiety is not interrupted or is interrupted by a carbonyloxy group, or biologically inactive steroid alcohols bonded via their hydroxyl groups, there being random distribution in the polymer of the monomer units placed in square brackets.

2. A method according to claim 1 wherein a biologically active substance is encapsulated by said controlled release agent.

3. A method according to claim 1 wherein the controlled release agent further contains other biodegradable and/or biocompatible polymers or physiologically acceptable auxiliaries.

4. A method according to claim 1 wherein the controlled release agent further contains physiologically acceptable polymer plasticizers.

* * * * *